United States Patent
Wu

(10) Patent No.: US 6,491,944 B2
(45) Date of Patent: Dec. 10, 2002

(54) METHOD FOR MAKING SPIRILLICIDE

(76) Inventor: Shian Shyang Wu, P.O. Box 10-69, Chong Ho, Taipei (TW), 235

( * ) Notice: Subject to any disclaimer, the term of this patent is extended or adjusted under 35 U.S.C. 154(b) by 82 days.

(21) Appl. No.: 09/828,730

(22) Filed: Apr. 6, 2001

(65) Prior Publication Data

US 2002/0146464 A1 Oct. 10, 2002

(51) Int. Cl.⁷ ............ A61K 47/00; A61K 9/20; A61K 9/14
(52) U.S. Cl. .......... 424/439; 424/464; 424/465; 424/489
(58) Field of Search ................ 424/464, 465, 424/489, 439

(56) References Cited

FOREIGN PATENT DOCUMENTS

JP 1997-290123 * 6/1995 ............ A61K/7/32

* cited by examiner

Primary Examiner—Thurman K. Page
Assistant Examiner—Humera N. Sheikh

(57) ABSTRACT

A method for making spirillicide includes mixing a chloride hydrargyrum ($Hg_2Cl_2$) material and a gypsum material and pork into particles, and the particles are then fried into pills. The chloride hydrargyrum ($Hg_2Cl_2$) material and the gypsum material are preferably ground into a mixed powder material before mixing with the pork, and may be fried with the sesame oil, or the peanut oil, or the soybean oil. The fried particles may be cooled into the room temperature under the room temperature, and may be refrigerated into the pills.

8 Claims, 2 Drawing Sheets

METHOD FOR MAKING SPIRILLICIDE

BACKGROUND OF THE INVENTION

1. Field of the Invention

The present invention relates to a method, and more particularly to a method for making spirillicide.

2. Description of the Prior Art

Various kinds of typical diseases, such as the syphilis, are constituted or formed by spirilla which may decompose the human tissue, such as the skin of people, and which may infect the other people. Various kinds of medicines have been developed as spirillicide. However, actually, the so-called spirillicide may be used for restraining purposes and may not be used for actually killing the spirilla.

The present invention has arisen to mitigate and/or obviate the afore-described disadvantages of the conventional spirillicide.

SUMMARY OF THE INVENTION

The primary objective of the present invention is to provide a method for making spirillicide that may be used for killing spirilla.

In accordance with one aspect of the invention, there is provided a method for making spirillicide, the method comprising mixing a chloride hydrargyrum ($Hg_2Cl_2$) material and a gypsum material and pork into particles, and frying the particles into pills.

A grinding process is further provided for grinding the chloride hydrargyrum ($Hg_2Cl_2$) material and the gypsum material into a mixed powder material.

The mixed powder material are then mixed with the pork and formed into the particles.

The frying process includes frying the particles with sesame oil, or with the peanut oil, or with the soybean oil.

A cooling process is further provided for cooling the fried particles, and a refrigerating process may further be provided for refrigerating the fried particles into the pills.

Further objectives and advantages of the present invention will become apparent from a careful reading of a detailed description provided hereinbelow, with appropriate reference to accompanying drawings.

DETAILED DESCRIPTION OF THE PREFERRED EMBODIMENT

Figure 1:
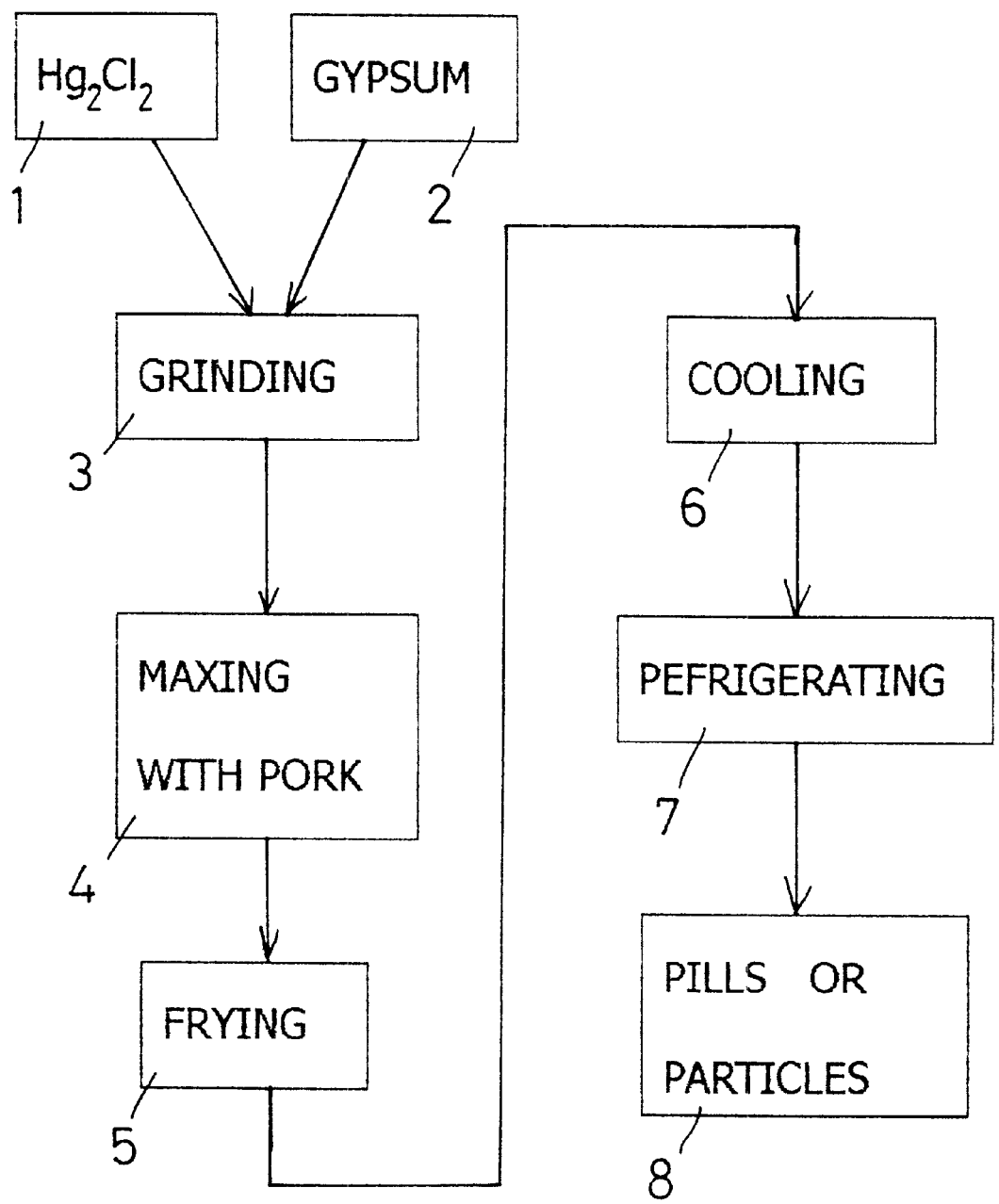
FIG. 1 is a block diagram showing a method for making spirillicide in accordance with the present invention.

Referring to the drawings, and initially to FIG. 1, a method for making spirillicide in accordance with the present invention comprises preparing (1) a chloride hydrargyrum ($Hg_2Cl_2$) powder, and preparing (2) a gypsum material, and grinding (3) the chloride hydrargyrum ($Hg_2Cl_2$) powder and the gypsum material into mixed powder material, and mixing (4) the mixed powder material with pork, particularly the raw pork, and formed into pills or particles.

Figure 2:
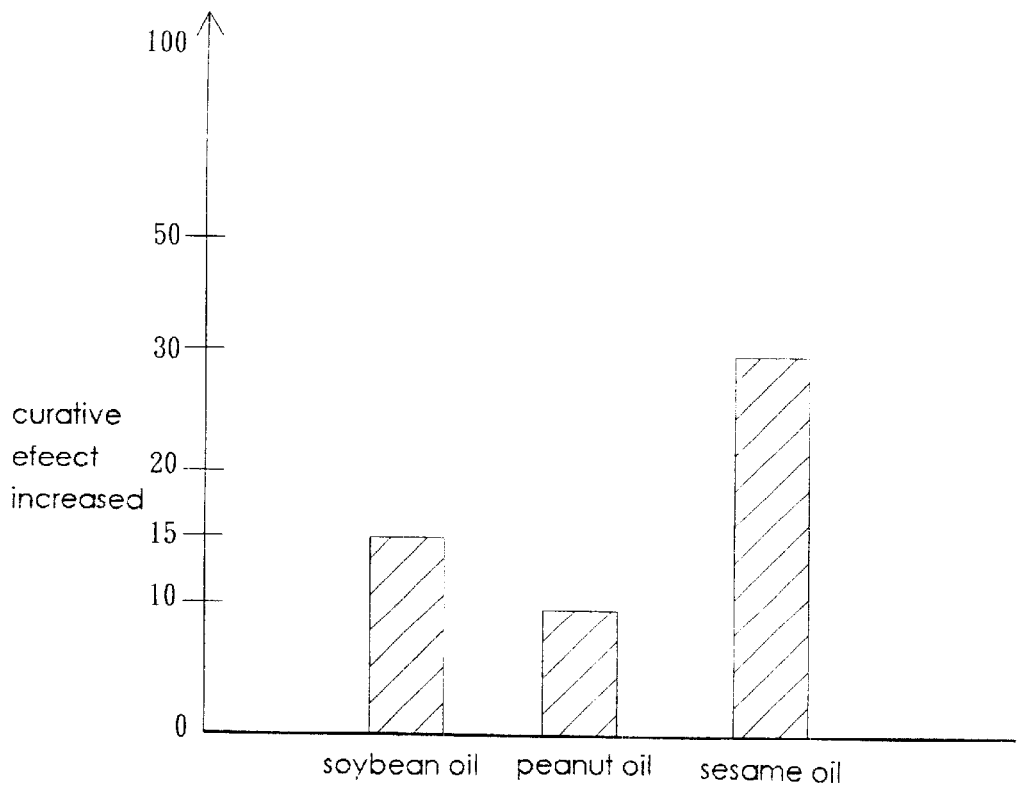
FIG. 2 is a chart illustrating the effect derived from different oils used.

The particles are then fried (5) in an oil, such as, as shown in FIG. 2, the sesame oil, the peanut oil, the soybean oil, or the like, until the pork is well cooked. The fried particles may include a slightly fried yellow color. The fried particles are then cooled (6) under such as the room temperature, for about one hour, until the fried particles have been cooled to the room temperature. The cooled particles are then refrigerated (7) so as to form the final particles or the pills (8). It is preferable that the pills (8) each weights about 0.12 g.

Figure 3:
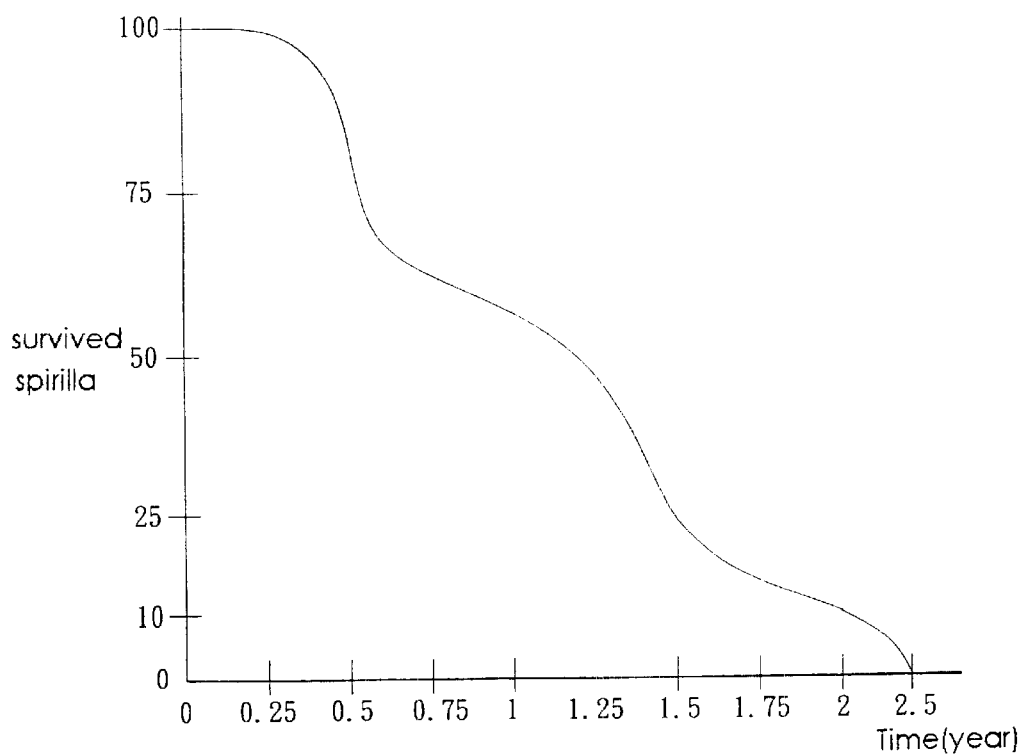
FIG. 3 is a chart illustrating the spirilla killing effect of the spirillicide made by the method in accordance with the present invention.

Referring next to FIG. 3, when a patient consumes five (5) pills 8 a day, the spirilla may be completely killed in two and a half (2.5) years. As shown in FIG. 2, the sesame oil includes a great proportion of sesame phenols which may promote or increase the killing effect against the spirilla which may be discharged out of the patient via the urine, the droppings, or the like. Accordingly, the sesame oil may include a better killing effect against the spirilla than the other oils (FIG. 2).

The chloride hydrargyrum ($Hg_2Cl_2$) powder may be become a solvable hydrargyrum material which may stimulate the stomach of the patient, and may cause or promote the wriggling of the stomach and may promote the internal secretion, after the spirilla have been killed by the spirillicide. The grease or the oil of the pork may protect the stomach for preventing the stomach from being damaged or over-stimulated by the solvable hydrargyrum material of the chloride hydrargyrum ($Hg_2Cl_2$) powder. The gypsum may be used for heat dissipating purposes for the patients for decreasing or for removing the heat generated in the patients.

Accordingly, the method in accordance with the present invention may be used for making spirillicide that may effectively kill spirilla.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A method for making spirillicide, said method comprising:

mixing a chloride hydrargyrum material and a gypsum material and pork into particles, and frying said particles into pills.

2. The method according to claim 1 further comprising grinding said chloride hydrargyrum material and said gypsum material into a mixed powder material.

3. The method according to claim 2 further comprising mixing said mixed powder material with said pork and forming into said particles.

4. The method according to claim 1, wherein said frying process includes frying said particles with sesame oil.

5. The method according to claim 1, wherein said frying process includes frying said particles with peanut oil.

6. The method according to claim 1, wherein said frying process includes frying said particles with soybean oil.

7. The method according to claim 1 further comprising cooling said fried particles.

8. The method according to claim 1 further comprising refrigerating said fried particles into said pills.

* * * * *